United States Patent
Agarwal et al.

(10) Patent No.: US 11,238,562 B2
(45) Date of Patent: Feb. 1, 2022

(54) ULTRASOUND SYSTEM WITH DEEP LEARNING NETWORK FOR IMAGE ARTIFACT IDENTIFICATION AND REMOVAL

(71) Applicant: KONINKLIJKE PHILIPS N. V., Eindhoven (NL)

(72) Inventors: Anup Agarwal, Mill Creek, WA (US); Keith William Johnson, Lynnwood, WA (US); Liang Zhang, Issaquah, WA (US); Earl M. Canfield, New Braunfels, TX (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 123 days.

(21) Appl. No.: 16/639,636

(22) PCT Filed: Aug. 2, 2018

(86) PCT No.: PCT/EP2018/070960
§ 371 (c)(1),
(2) Date: Feb. 17, 2020

(87) PCT Pub. No.: WO2019/034436
PCT Pub. Date: Feb. 21, 2019

(65) Prior Publication Data
US 2020/0175652 A1 Jun. 4, 2020

Related U.S. Application Data

(60) Provisional application No. 62/546,588, filed on Aug. 17, 2017.

(51) Int. Cl.
*G06T 5/00* (2006.01)
*G06T 7/246* (2017.01)
(Continued)

(52) U.S. Cl.
CPC .............. *G06T 5/002* (2013.01); *A61B 8/085* (2013.01); *A61B 8/0891* (2013.01);
(Continued)

(58) Field of Classification Search
CPC ......... G06T 5/002; G06T 5/001; G06T 5/246; G06T 5/20; G06T 5/005; G06T 5/10;
(Continued)

(56) References Cited

U.S. PATENT DOCUMENTS 9,351,708 B2   5/2016  Anand et al.
10,610,203 B2 * 4/2020  Liang ..................... A61B 8/461
(Continued)

FOREIGN PATENT DOCUMENTS

EP    2830502 A1    2/2015
WO    2013144912 A1    10/2013

OTHER PUBLICATIONS

International Search Report and Written Opinion for International Application No. PCT/EP018/070960, filed Aug. 2, 2018, 13 pages.
(Continued)

*Primary Examiner* — Jose L Couso

(57) ABSTRACT

An ultrasound system with a deep learning neural network feature is used to eliminate haze artifacts in B mode images of the carotid artery by analysis of orthogonal information. In a described implementation the orthogonal information comprises the structural information of a B mode image and motion information of the same field of view as that of the B mode image. In another embodiment the neural network reduces haze artifacts by reducing TGC gain at the depth of artifacts.

12 Claims, 8 Drawing Sheets

(51) Int. Cl.

| | |
|---|---|
| *G16H 50/20* | (2018.01) |
| *G16H 30/40* | (2018.01) |
| *A61B 8/08* | (2006.01) |
| *A61B 8/00* | (2006.01) |
| *G06K 9/62* | (2006.01) |
| *G06N 3/04* | (2006.01) |
| *G06N 3/08* | (2006.01) |
| *G06T 5/20* | (2006.01) |
| *G06T 7/00* | (2017.01) |

(52) U.S. Cl.
CPC ............ *A61B 8/4254* (2013.01); *A61B 8/488* (2013.01); *A61B 8/5246* (2013.01); *A61B 8/5276* (2013.01); *G06K 9/6217* (2013.01); *G06N 3/04* (2013.01); *G06N 3/08* (2013.01); *G06T 5/20* (2013.01); *G06T 7/0014* (2013.01); *G06T 7/246* (2017.01); *G16H 30/40* (2018.01); *G16H 50/20* (2018.01); *G06K 2209/05* (2013.01); *G06T 2207/10132* (2013.01); *G06T 2207/20081* (2013.01); *G06T 2207/20084* (2013.01); *G06T 2207/30101* (2013.01)

(58) Field of Classification Search
CPC ..... G06T 5/003; G06T 7/0014; G06T 7/0012; G06T 7/0016; G06T 7/215; G06T 7/32; G06T 2207/10132; G06T 2207/20081; G06T 2207/20084; G06T 2207/30101; G06T 2207/10121; G06T 2207/10136; G06T 2207/20182; G06T 2207/20012; G06T 2207/20076; G06T 2207/20192; G06T 2207/30004; G06T 2207/20004; G06T 2207/10016; G06T 2207/30168; G06T 2210/41; G16H 50/20; G16H 50/30; G16H 50/70; G16H 30/40; G16H 40/63; A61B 8/085; A61B 8/0891; A61B 8/4254; A61B 8/488; A61B 8/5246; A61B 8/5276; A61B 8/463; A61B 8/483; A61B 8/52; A61B 8/00; A61B 8/5269; A61B 8/12; A61B 8/4444; A61B 8/46; A61B 8/5223; A61B 8/5207; A61B 34/20; G06K 9/6217; G06K 9/00; G06K 9/6256; G06K 9/66; G06K 9/4628; G06K 9/6271; G06K 9/40; G06K 9/00577; G06K 9/627; G06K 9/628; G06K 9/46; G06K 9/6267; G06K 2209/05; G06N 3/04; G06N 3/0454; G06N 3/08–088; G06N 20/00; G01S 7/52077; G01S 7/52085; G01S 7/52066; G01S 15/8979

See application file for complete search history.

(56) References Cited

U.S. PATENT DOCUMENTS

| | | | |
|---|---|---|---|
| 2003/0187353 A1 | 10/2003 | Ng et al. | |
| 2009/0131788 A1 | 5/2009 | Settlemier et al. | |
| 2012/0078097 A1 | 3/2012 | Wang et al. | |
| 2013/0041260 A1* | 2/2013 | Schmidt | A61B 8/406 600/442 |
| 2013/0303880 A1* | 11/2013 | Hsu | A61B 5/015 600/411 |
| 2015/0080725 A1* | 3/2015 | Wegner | G01S 15/8997 600/440 |
| 2015/0133784 A1* | 5/2015 | Kapoor | A61B 8/4254 600/438 |
| 2016/0058425 A1* | 3/2016 | Wong | A61B 8/5276 600/453 |
| 2016/0239959 A1* | 8/2016 | Blackbourne | G06T 7/0012 |
| 2016/0328998 A1* | 11/2016 | Pedersen | A61B 8/4254 |
| 2016/0350620 A1* | 12/2016 | Rao | G06T 5/001 |
| 2017/0340310 A1* | 11/2017 | Carlini | A61B 8/0825 |
| 2018/0028146 A1* | 2/2018 | Zhang | A61B 8/483 |
| 2018/0177461 A1* | 6/2018 | Bell | A61B 5/0095 |

OTHER PUBLICATIONS

Lekadir, et al., "A Convolutional Neural Network for Automatic Characterization of Plaque Composition in Carotid Ultrasound", IEEE Journal of Biomedical and Health Informatics, vol. 21, No. 1, Jan. 2017, pp. 48-55.

Naik, et al., "Carotid Artery Segmentation in Ultrasound Images and Measurements of Intima-Media Thickness", Hindawi Publishing Corporation, BioMed Research International, vol. 2013, Article ID 801962, 10 pages.

Pazinato, et al., "Pixel-Level Tissue Classification for Ultrasound Images", IEEE Journal of Biomedical and Health Informatics, vol. 20, No. 1, Jan. 2016, pp. 256-267.

* cited by examiner

ULTRASOUND SYSTEM WITH DEEP LEARNING NETWORK FOR IMAGE ARTIFACT IDENTIFICATION AND REMOVAL

RELATED APPLICATIONS

This application is the U.S. National Phase application under 35 U.S.C. §371 of International Application No. PCT/EP2018/070960, filed on Aug. 2, 2018, which claims priority to and the benefit of Provisional Application Ser. No. 62/546,588, filed Aug. 17, 2017. These applications are hereby incorporated by reference herein.

This invention relates to medical diagnostic ultrasound systems and, in particular, to ultrasound systems with deep learning networks which enhance ultrasound images by identifying image artifacts for removal.

Currently available medical ultrasound systems enable clinicians to conduct ultrasound scans on a patient using on-board exam protocols, capture images, make measurements and use built-in algorithms and report generation software to make diagnoses and report the results of a diagnosis. Prior to starting the exam, the clinician must set up the system by selecting the settings and functions to be used and performed during the exam. This usually starts with selecting the probe type to be used, then the exam type (OB, cardiology, peripheral vascular, etc.), followed by an exam protocol when one is to be used, and other ultrasound machine operating settings. Present day ultrasound systems have automated exam setups, which can be selected from an onboard list of common exams or settings saved from one exam and invoked for a subsequent exam at the press of a button. See, for instance, U.S. Pat. No. 5,315,999 (Kinicki et al.) The manufacturers of these systems have evolved this feature into systems having what are known as "tissue specific presets." These are factory-installed presets typically used in the various types of ultrasound exams which can be invoked on the system by pressing a single button. For instance, an obstetrician preparing to perform a fetal exam of an expectant mother can press the "OB" button and the ultrasound system is immediately conditioned with settings typically used for the performance of a fetal exam.

Deep learning is a rapidly developing branch of machine learning algorithms that mimic the functioning of the human brain in analyzing problems. The human brain recalls what was learned from solving a similar problem in the past, and applied that knowledge to solve a new problem. Exploration is underway to ascertain possible uses of this technology in a number of areas such as pattern recognition, natural language processing and computer vision. Deep learning algorithms have a distinct advantage over traditional forms of computer programming algorithms in that they can be generalized and trained to recognize image features by analyzing image samples rather than writing custom computer code. The anatomy visualized in an ultrasound system would not seem to readily lend itself to automated image recognition, however. Every person is different, and anatomical shapes, sizes, positions and functionality vary from person to person. Furthermore, the quality and clarity of ultrasound images will vary even when using the same ultrasound system. That is because body habitus will affect the ultrasound signals returned from the interior of the body which are used to form the images. Scanning an organ through thick layers of body fat will result in greatly attenuated ultrasound signals and poorly defined anatomy in the images. Nevertheless, the system described in this application has demonstrated the ability to use deep learning technology to recognize anatomy in ultrasound images through processing by a neural network model. The neural network model is first trained by presenting to it a plurality of images of known anatomy. Once trained, saved or live images acquired by a user are analyzed by the neural net model in real time, which identifies the anatomy in the images. The identification of the anatomy is used to annotate the image, or set up the user controls on the ultrasound system for the conduct of an exam of the identified anatomy.

Having demonstrated the ability to recognize anatomy in ultrasound images, a further desire in the use of deep learning is to use it to improve image quality. One diagnostic area where this would be of benefit is in the detection and analysis of plaque which has formed in blood vessels. Plaque is often only faintly visible in ultrasound images of blood vessels, and is difficult to detect. This difficulty is compounded by the physics and anatomy of blood vessels, which can reflect ultrasound from the walls of a blood vessel in the form of reverberations and other multi-path reflections. These reverberations will be detected by the ultrasound transducer and manifest themselves in the ultrasound image as a haze (clutter) over the vessel, which can obscure plaque buildup on the vessel walls, as the clutter generally appears in the same brightness range as plaque. It would be desirable to be able to use a feature such as deep learning to analyze ultrasound images, recognize image artifacts such as haze from reverberation and other multi-path distortion, and remove it from the image so that plaque can be more reliably diagnosed. It is further desirable to be able to detect and remove such artifacts without significantly affecting the time required to acquire and process the ultrasound images, so that the image frames can be presented in a real time display to the user.

In accordance with the principles of the present invention, an ultrasound system acquires a B mode image of a region of the body and orthogonal information of the same region. By orthogonal is meant a second source of information of the anatomy which complements the structural information of a B mode image, such as motion. The B mode image or the B mode image and the orthogonal information is analyzed by a neural network model which has been trained for this purpose, identifying haze artifacts in the image in contradistinction to anatomical material such as plaque. The identified artifacts are then removed from the image as by filtering. In another implementation, the neural network model identifies a blood vessel and haze or clutter in the vessel, then reduces the TGC (time gain control) gain at the image depth of the haze or clutter to eliminate it from the image.

Figure 1:
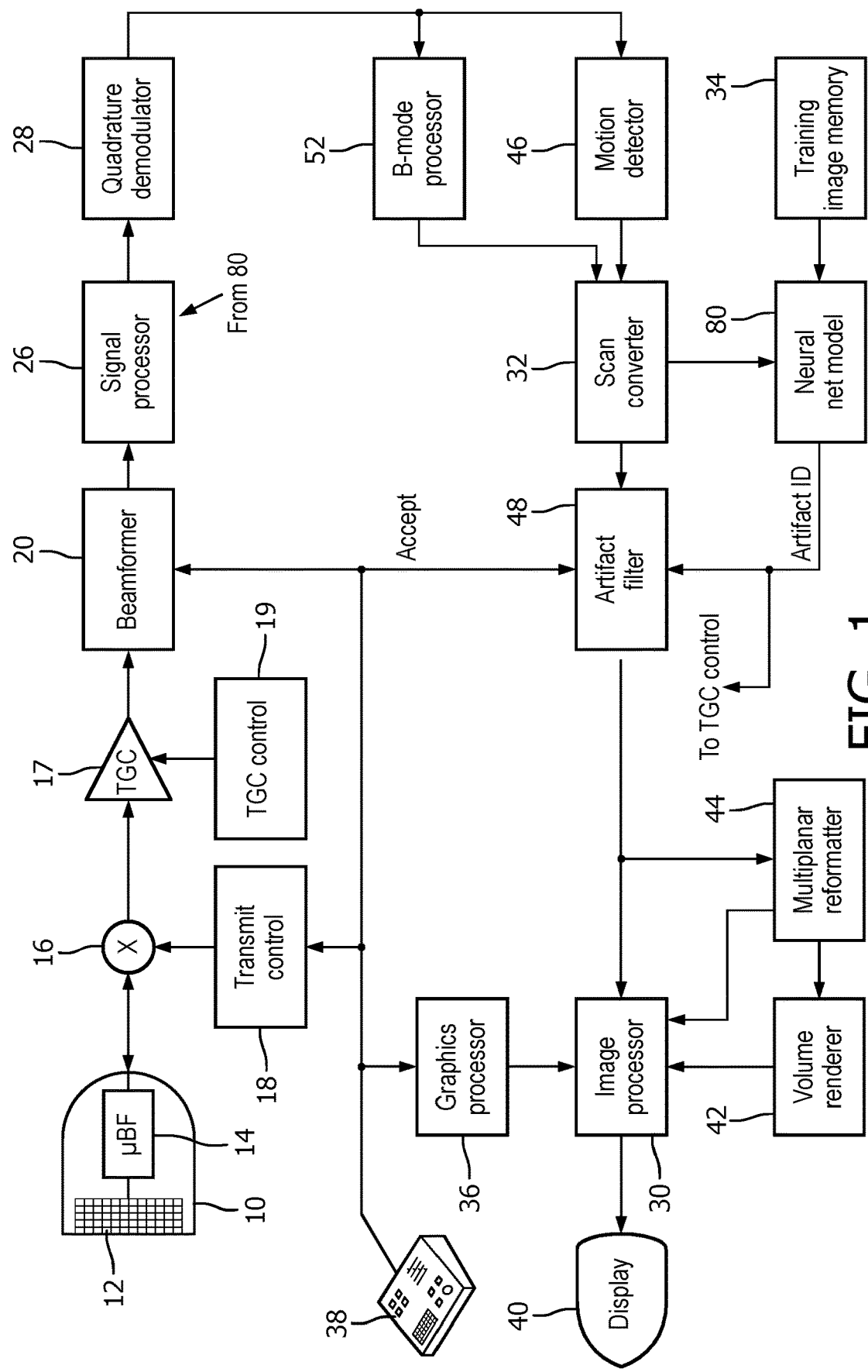
FIG. 1 illustrates an ultrasound system configured in accordance with the principles of the present invention.

Referring now to FIG. 1, an ultrasonic diagnostic imaging system constructed in accordance with the principles of the present invention is shown in block diagram form. A transducer array 12 is provided in an ultrasound probe 10 for transmitting ultrasonic waves and receiving echo information. The transducer array 12 may be a one- or two-dimensional array of transducer elements capable of scanning in two or three dimensions, for instance, in both elevation (in 3D) and azimuth. The transducer array 12 is coupled to a microbeamformer 14 in the probe which controls transmission and reception of signals by the array elements. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer is coupled by the probe cable to a transmit/receive (T/R) switch 16 which switches between transmission and reception and protects the main beamformer 20 from high energy transmit signals. The transmission of ultrasonic beams from the transducer array 12 under control of the microbeamformer 14 is directed by a transmit controller 18 coupled to the T/R switch and the beamformer 20, which receives input from the user's operation of the user interface or control panel 38. Among the transmit characteristics controlled by the transmit controller are the spacing, amplitude, phase, and polarity of transmit waveforms. Beams formed in the direction of pulse transmission may be steered straight ahead from the transducer array, or at different angles for a wider field of view.

The echoes received by the transducer array 12 are amplified as a function of depth in the subject by TGC amplifiers 17 under control of TGC control circuitry 19. Time gain control compensation has been used in ultrasound for many years. The amplifier gain may be set by graphic touchscreen controls on the display or by mechanical slidepots as described in U.S. Pat. No. 5,482,045 (Rust et al.) incorporated herein by reference. The slidepot adjustments made manually are applied directly to the TGC amplifiers or gain values stored in memory of the TGC control circuitry and used to control the gain. The gain-compensated echoes received by a contiguous group of transducer elements are beamformed by appropriately delaying them and then combining them. The partially beamformed signals produced by the microbeamformer 14 from each patch are coupled to a main beamformer 20 where partially beamformed signals from individual patches of transducer elements are combined into a fully beamformed coherent echo signal. For example, the main beamformer 20 may have 128 channels, each of which receives a partially beamformed signal from a patch of 12 transducer elements. In this way the signals received by over 1500 transducer elements of a two-dimensional array transducer can contribute efficiently to a single beamformed signal.

The coherent echo signals undergo signal processing by a signal processor 26, which includes filtering by a digital filter and noise reduction as by spatial or frequency compounding. The signal processor can also shift the frequency band to a lower or baseband frequency range. The digital filter of the signal processor 26 can be a filter of the type disclosed in U.S. Pat. No. 5,833,613 (Averkiou et al.), for example. The processed echo signals then are demodulated into quadrature (I and Q) components, which provide signal phase information.

The beamformed and processed coherent echo signals are coupled to a B mode processor 52 which produces a B mode image of structure in the body such as tissue. The B mode processor performs amplitude (envelope) detection of quadrature demodulated I and Q signal components by calculating the echo signal amplitude in the form of $(I^2+Q^2)^{1/2}$. The quadrature echo signal components are also coupled to a motion detector 46. In one implementation of the present invention, the motion detector comprises a Doppler processor, which stores ensembles of echo signals from discrete points in an image field which are then used to estimate the Doppler shift at points in the image with a fast Fourier transform (FFT) processor. The Doppler shift is proportional to motion at points in the image field, e.g., blood flow and tissue motion. For a color Doppler image, the estimated Doppler flow values at each point in a blood vessel are wall filtered and converted to color values using a look-up table. The B mode image signals and the Doppler flow values are coupled to a scan converter 32 which converts the B mode and Doppler samples from their acquired R-θ coordinates to Cartesian (x,y) coordinates for display in a desired display format, e.g., a rectilinear display format or a sector display format as shown in FIGS. 2, 3, 4a and 4b. Either the B mode image or the Doppler image may be displayed alone, or the two shown together in anatomical registration in which the color Doppler overlay shows the blood flow in tissue and vessels in the image as shown in FIG. 4b.

In accordance with the principles of the present invention the B mode image information and orthogonal information of the same image region are coupled to a neural net model 80, which analyzes the two types of information using principles of deep learning. Deep learning neural net models comprise software which may be written by a software designer, and are also publicly available from a number of sources. In the ultrasound system of FIG. 1, the neural net model software is stored in a digital memory. An application which can be used to build a neural net model called "NVidia Digits" is available at https://developer.nvidia.com/digits. NVidia Digits is a high level user interface around a deep learning framework called "Caffe" which has been developed by the Berkley Vision and Learning Center, http://caffe.berkeleyvision.org/. A list of common deep learning frameworks suitable for use in an implementation of the present invention is found at https://developer.nvidia.com/deep-learning-frameworks. Coupled to the neural net model 80 is a training image memory 34, in which ultrasound images of known patient anatomy are stored and used to train the neural net model to identify artifacts in ultrasound images of that anatomy from orthogonal image information. Live images produced by the ultrasound system of FIG. 1, such as the carotid artery images of FIGS. 2, 3, 4a and 4b are presented to the neural net model during training of the model to identify artifacts such as haze artifacts in images of the carotid artery from orthogonal information, e.g., B mode (structural) information and motion information. In a constructed implementation of the present invention, the neural net model was trained to identify haze artifacts in ultrasound images of the carotid artery using orthogonal information. The trained neural net model analyzes this information and, where image artifacts are identified, produces "Artifact ID" data identifying the location of the artifact in the image field, and also produces a confidence factor of what the model estimates as the accuracy of its identification, e.g., 80% confident, 100% confident, or some other factor. The confidence factor is displayed on the display screen of the ultrasound system, where the user may take this factor into consideration when deciding whether to accept the image analysis performed by the neural net model and its subsequent use to filter out any identified artifacts. When the neural net model analysis is accepted, the Artifact ID data is applied to an artifact filter 48, which uses the data to remove artifacts from the B mode image produced by the scan converter 32. The artifact filter may take various forms. It may be a pixel-by-pixel filter which removes (darkens) pixels at pixel locations in a blood vessel identified by the Artifact ID as being haze or other artifacts. The filter may apply a reduced TGC (time gain control) at image locations identified by the Artifact ID data as containing artifacts, as described more fully below. The filter 48 may apply spatially selective smoothing to regions of the B mode image. The filter 48 can perform different grayscale compression or temporal filtering to image regions identified as containing artifacts. Another alternative is to use the Artifact ID data to vary the r.f. signal as by adjusting the passband of a bandpass filter of the signal processor 26.

The improved ultrasound images produced by the artifact filter 48 are coupled to an image processor 30 and a multiplanar reformatter 44. The multiplanar reformatter converts echoes which are received from points in a common plane in a volumetric region of the body into an ultrasonic image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.) The 2D or 3D images are coupled to an image processor 30 for further enhancement, buffering and temporary storage for display on an image display 40. A graphic display overlay containing textual and other graphic information such as patient ID is produced by a graphics processor 36 for display with the ultrasound images.

Figure 2:
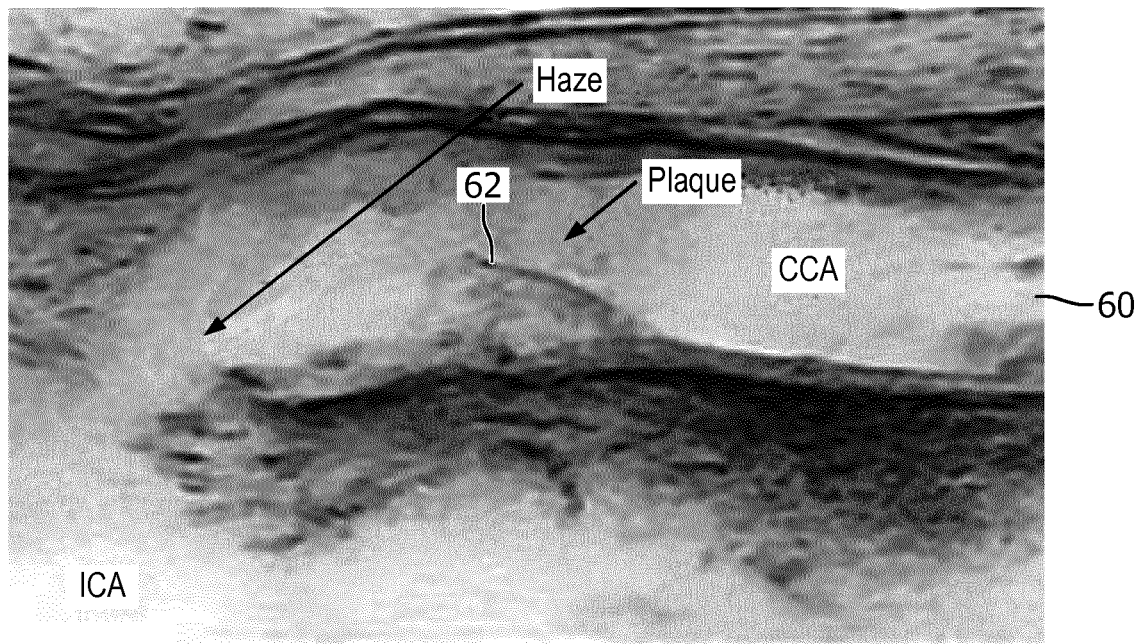
FIGS. 2 and 3 illustrate ultrasound images of blood vessels containing both haze artifacts and plaque.

FIG. 2 illustrates one example of an ultrasound B mode image of a carotid artery 60 which contains both plaque and multipath haze artifacts in the lumen of the artery in the image. Indicated at 62 is a buildup of plaque on the wall of the common carotid artery (CCA). Just to the left of the location of the plaque is a region darkened (in this image which is shown with black/white reversal for ease of illustration; in a standard ultrasound image, it will be brightened) by haze artifact just before the artery branches into the internal carotid artery. The close proximity of the haze to the target plaque can make the plaque difficult to detect and its boundaries difficult to distinguish in the image.

Figure 3:
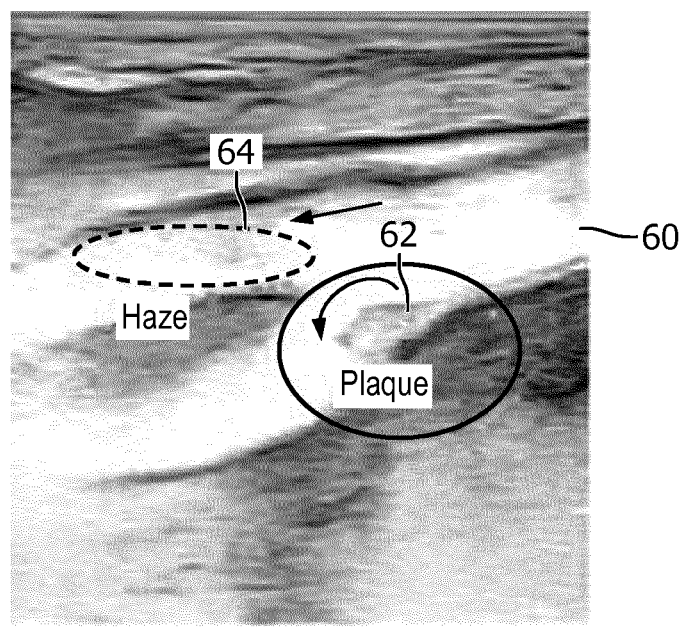

FIG. 3 is a second illustration of an ultrasound B mode image of a carotid artery 60 which contains both plaque 62 and multipath haze artifacts 64 in the lumen of the artery. In this example both are near a bifurcation of the artery, with the plaque at the entry to the lower branch and the haze at the entry to the upper branch. In this image the darkness (brightness) of the haze 64 could be mistaken for possible plaque during diagnosis. This example also illustrates the benefit of the use of orthogonal information, in this case, the motion of flow, which is not found in a B mode image. The partial obstruction of the entry to the lower branch of the carotid caused by the plaque makes the lumen narrower at this location, as the flow of blood has to go around the plaque to enter the lower branch, as indicated by the curved arrow. A colorflow image of the blood flow at this location would show an increase in the flow velocity around the plaque, and also turbulence resulting from the redirected blood flow. This is distinctly different from the flow of blood in the upper branch of the vessel where the haze is located. Blood flow in this region will be normal straight laminar flow as indicated by the heavier arrow. The blood flow is not impeded or affected by the haze since the haze is not structural but is simply an artifact of the ultrasound signals and their processing. Thus, the combination of the structural information of a B mode image and motion information about the same region can lead to the identification and elimination of the haze artifact in the image.

Figure 4A:
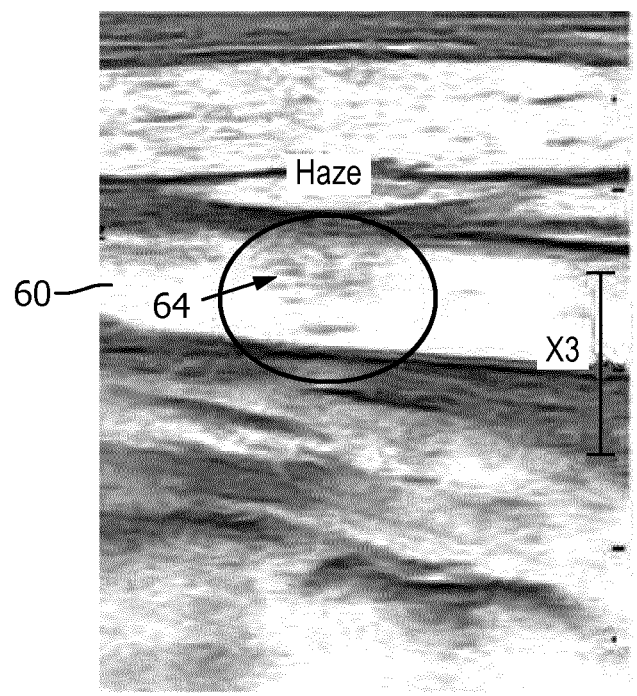
FIGS. 4a and 4b illustrate ultrasound images of orthogonal information of the same anatomy, haze artifact in a B mode image of a blood vessel and motion (flow) in a colorflow image of the same blood vessel.
Figure 4B:
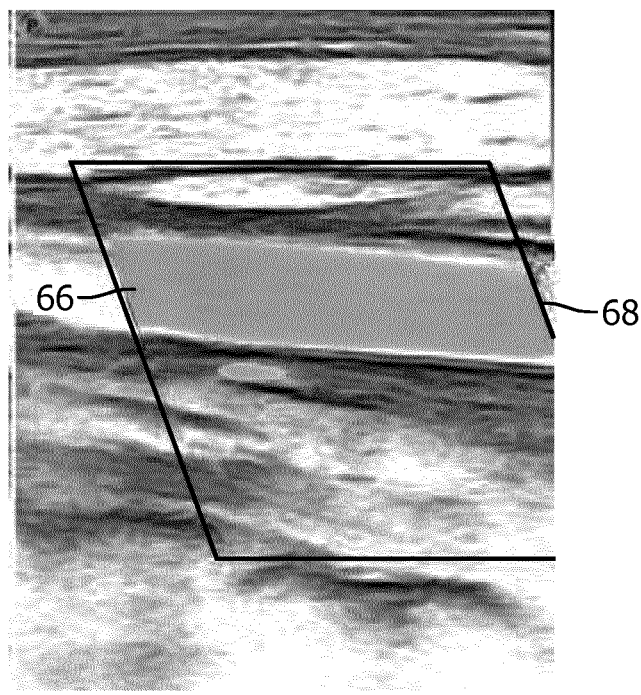

FIGS. 4*a* and 4*b* illustrate two ultrasound images of the same image region of a carotid artery 60 but with different image information in a side-by-side presentation. The B mode image on the left is seen to be cluttered with haze artifacts 64 in the carotid, but the colorflow image on the right shows that the carotid lumen contains smoothly flowing blood as shown by the uniform flow color 66 in the colorflow box 68, revealing that the contaminated area is haze artifact and not flow-altering plaque. A diagnosis could be made from these two side-by-side images, but that would require the acquisition of ensembles of echo samples from each point in the colorflow box 68, which requires repeated transmits over the area of the box. These repeated transmits and their resulting echoes, the speed of which is limited by the speed of sound in the body (approximately 1,540 m/sec) for each transmit-receive interval, increases time required to acquire the ensembles of echoes needed for Doppler flow estimation and hence the time required to acquire each new colorflow image. This results in a reduction of the frame rate of display of the images and diminishes the ability to display the carotid images as a real time display. This time can be shortened by decreasing the ensemble length, the number of interrogations of each point in the colorflow box, but this reduces the accuracy of the displayed motion of flow. In accordance with the present invention, this dilemma is overcome by using acquisition which requires fewer transmit-receive cycles and analyzing both sets of image data, B mode and motion information, with the neural net model which operates at the speed of a computer. It has been found that even with a reduction in the interrogation of the motion field, a trained neural net model can still identify haze artifacts with high confidence levels. For example, a full acquisition of relatively long ensembles of echo signals, six or more samples, will require a certain long acquisition time. This time can be reduced by using multiline acquisition, in which multiple adjacent scanlines of echo samples are acquired in response to a single broad transmit beam, as described in U.S. Pat. No. 8,137,272 (Cooley et al.) Even though the resolution of such data is diminished as opposed to a single standard line-by-line acquisition, it has been found sufficient for artifact identification by the neural net model analysis. Another approach to reducing acquisition time is to use shorter ensemble lengths of less than six samples, which has also been found to be sufficient for successful deep learning analysis. Yet another way to detect the motion information is by speckle tracking, in which the speckle characteristics of at least two interrogations of a region are compared. Speckle is a phenomenon of ultrasound images of tissue which arise due to the coherent nature of ultrasound. Ultrasound scattered from tissue will exhibit a unique pattern due to the interaction of the relative phases of the scattered signals, producing a pattern which does not change from one image to another in the absence of motion (probe or tissue motion). The speckle patterns of two consecutively acquired images can be subtracted, resulting in virtually complete cancellation when the signals are returned from tissue. But the signals returned from flowing blood are constantly changing due to the motion of the blood flow, resulting in a small residual signal after frame-to-frame subtraction. Thus, only two B mode interrogations of an image field can provide information as to which areas are structural (tissue, plaque) and which are not (blood flow). The need for only a few such interrogations reduces the transmit-receive cycles needed for acquisition of both types of information, structural and motion, which is the information needed for high confidence neural net model analysis of the two types of image data. The deep learning analysis, relying on computation by computer processing in the ultrasound system which is not limited by transmit-receive cycle times governed by the speed of sound, is relatively instantaneous compared to ultrasound acquisition. The resulting images can be updated and displayed in real time at a high frame rate of display with the haze artifacts eliminated with a high degree of confidence. This enables haze artifact elimination while performing other image enhancement which does require extended acquisition times, such as spatial compounding, all without an unacceptable reduction in the real time frame rate of display.

Figure 5:
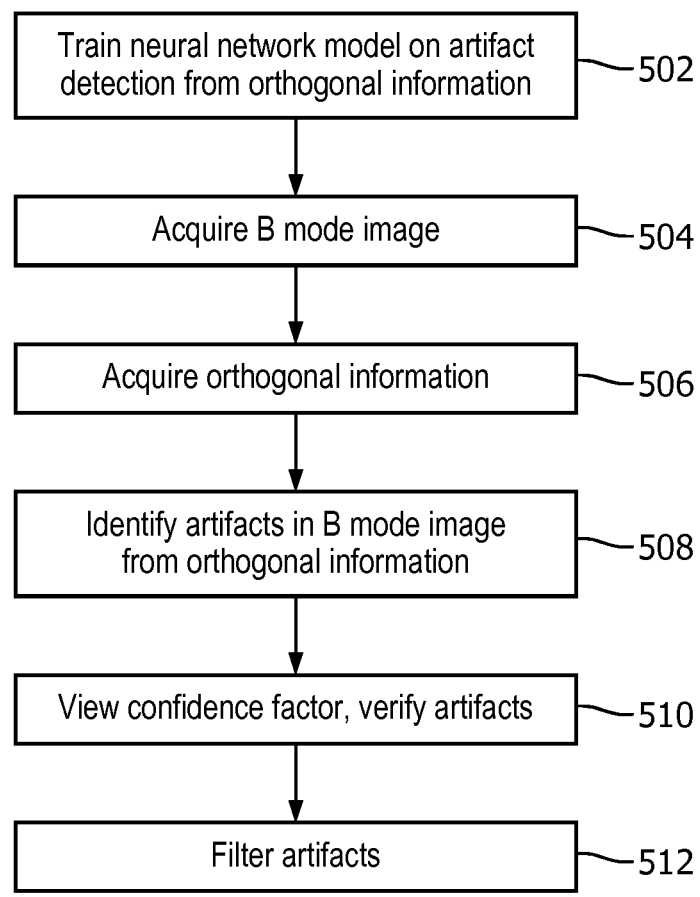
FIG. 5 is a flowchart illustrating a first method of improving image quality by removing image artifacts using orthogonal image information in accordance with the principles of the present invention.

A method for training and using a neural network model to identify and eliminate image artifacts using orthogonal image information is shown in FIG. 5. At the outset, a neural network model is installed on a computer-based ultrasound system. The neural network model may be one designed by a software architect, or may be one built using one of the deep learning frameworks available as described above. In step 502 images of carotid arteries containing both artifacts and plaque acquired from a plurality of patients are presented to the neural network model along with orthogonal image information such as motion in the image region to train the model to identify the artifacts and distinguish them from plaque. The number of training images used is preferably in the hundreds or thousands in order to train the neural network model in the variations of such image artifacts and structures and their differences as indicated by the orthogonal information. With the trained neural network model installed on an ultrasound system, B mode images are acquired by the ultrasound system in step 504 along with orthogonal information of the same region in step 506 and are presented to the neural network model for artifact identification. In step 508 the artifacts in the B mode images are identified by the neural network model using the orthogonal information, and a confidence factor is produced by the model. In step 510 the user views the confidence factor and, if satisfied with it, verifies the analysis which identified the artifacts. In step 512 the identified artifacts are removed from the B mode image using one of the filter techniques described above.

Figures 6, 6A:
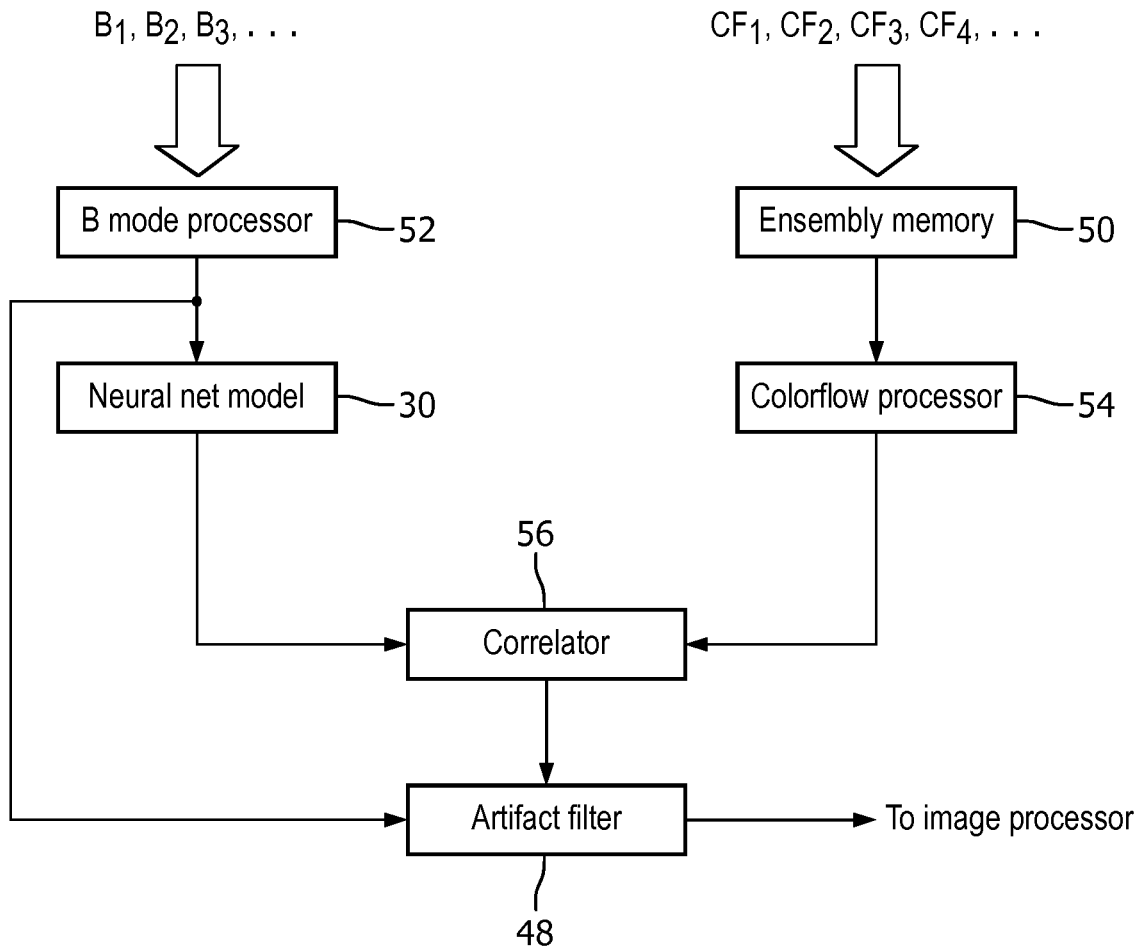
FIG. 6 illustrates a portion of the ultrasound system of FIG. 1 when reconfigured to remove image artifacts using orthogonal image information in a second way.
FIG. 6a is a table illustrating the operation of the correlator of FIG. 6.

A second implementation of the present invention is illustrated in FIG. 6, which is a reconfiguration of a portion of FIG. 1. The previous implementation uses a neural network model which was trained to identify artifacts in ultrasound images by analyzing orthogonal information, such as B mode images and corresponding motion (flow) images. This training is rather complex, as the neural network model must consider both types of corresponding images together. Furthermore, the availability of such corresponding image sets may be limited, affording an insufficient number of image sets for the desired degree of neural network training. The second implementation of FIG. 6 addresses this concern by using the neural network for the more limited task of identifying artifacts in B mode images alone. This means that the neural network is trained with just B mode images, a simpler approach, for which many more training images will generally be available. In the implementation of FIG. 6, frames of B mode data ($B_1$, $B_2$, $B_3$, . . . ) are acquired in interleaved sequence with colorflow frame data ($CF_1$, $CF_2$, $CF_3$, $CF_4$, . . . ). Each set of B mode frame data is processed to form a B mode image by a B mode processor 52. The sets of colorflow frame data are stored in an ensemble memory 50, where data ensembles of a desired length for Doppler estimation are assembled. When ensembles of the desired length have been assembled, they are processed by a colorflow processor 54 to produce a colorflow image. The colorflow image can be a flow velocity image, and it can also be a power Doppler image of Doppler signal intensity at each pixel location.

The neural network model 80 in this implementation has been trained with B mode images to identify artifacts in such images. The B mode images produced by the B mode processor 52 are analyzed by neural network model 80 for artifacts, and the results of this analysis are coupled to a correlator 56, which also receives the colorflow information of the same image region from colorflow processor 54. The function of correlator 56 is to see how well these two types of orthogonal information correlate throughout the region of the B mode image. This is illustrated by the table in FIG. 6a. For instance, if the neural network model has identified image information of a pixel of the B mode image with a high degree of accuracy (e.g., a 100% confidence factor), and the colorflow processor has identified the image information of the spatially corresponding pixel in the colorflow image as complementary with the same accuracy, then the two are seen to be highly correlated. For example, the neural network model may identify a pixel as tissue and if the colorflow image has found no flow at that pixel location, the two results from the orthogonal data are highly correlated. The tissue pixel in the B mode image will remain unchanged (N.C.=no change). For another example, the neural network model may find no tissue at a pixel location with high confidence, and the colorflow image may find blood flow at the same spatial pixel location. These two results correlate, and the pixel will be unchanged in the B mode image; a lumen of a blood vessel where blood is present is usually displayed in black. As yet another example, the neural network model may identify a pixel in the B mode image as being artifact, and the colorflow image may show blood flow at that pixel location with a high degree of accuracy. These two outcomes correlate, meaning that the artifact should be removed (Del.=delete) by the artifact filter 48. The artifact filter uses this outcome of the correlation to remove the artifact from the B mode image, and the fully filtered image is then forwarded to the image processor 30 for display.

With the ultrasound system operating to remove image artifacts with this degree of effectiveness, it may be decided to increase the frame rate of display. This may be done by acquiring fewer frames of colorflow data ($CF_n$) which will mean ensemble lengths will be shorter, for instance, or acquiring the B mode images with more widely spaced and hence fewer scanlines. Both of these changes will decrease the time required to acquire image data and hence improve the display frame rate, but at the possible cost of reduced effectiveness in artifact elimination. For instance, as a result of these changes, the neural network model may identify artifacts in the B mode images with only an 80% degree of confidence, and blood flow may be detected with only a 10% degree of accuracy as shown at the bottom of the table in FIG. 6a. The result of the comparison of the orthogonal data may be inconclusive, a low degree of correlation. With an inconclusive outcome, the decision may be to do nothing to the image as indicated by the ⇆ arrows, and the image may thereby contain undeleted artifacts. The user may decide to accept the possibility of greater artifact contamination because the diagnostic benefit of the higher frame rate of display is greater. Or, the user may decide to accept a lower frame rate of display in order to have more artifact-free images. But the speed of the neural network model analysis is in any event a function of the computational speed of the ultrasound system and not a significant detriment to frame rate as is an increase in the colorflow frames necessary to improve the colorflow performance. The performance of the neural network analysis will remain high even as colorflow ensembles are lengthened.

Figure 7:
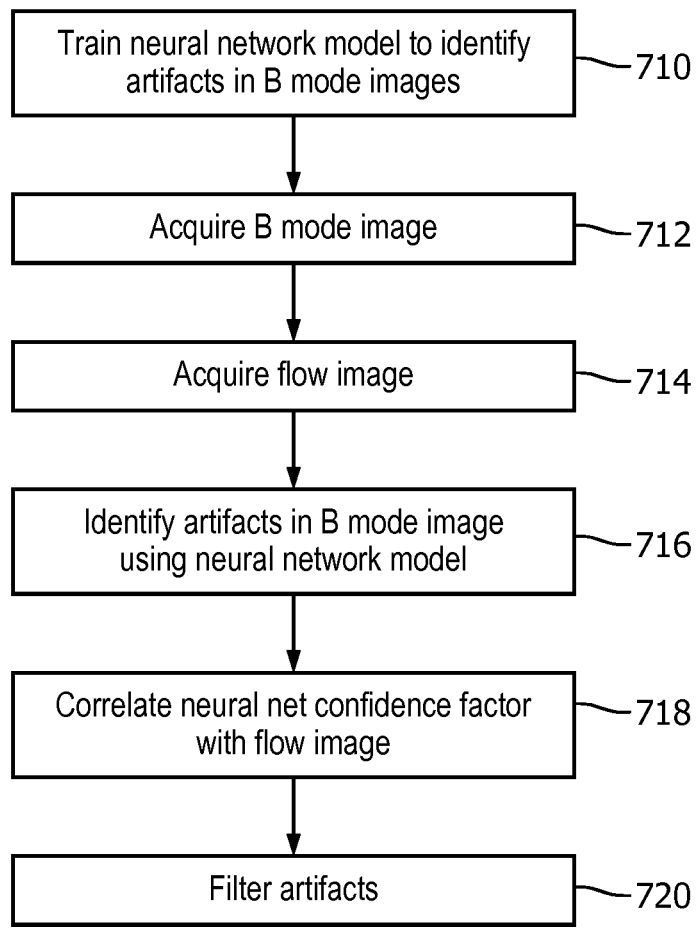
FIG. 7 is a flowchart illustrating a second method of improving image quality by removing image artifacts using orthogonal image information in accordance with the subsystem of FIG. 6.

FIG. 7 is a flowchart of the operation of this second implementation of the present invention. In step 710 the neural network model is trained to identify artifacts such as reverberation artifacts in B mode images. In step 712 one or more B mode images are acquired and in step 714 one or more flow images are acquired. Steps 712 and 714 are repeated with an interleave sequence desired to acquire sufficient flow data for the desired precision of Doppler flow estimation; longer ensembles will result in greater precision. In step 716 the artifacts in a B mode image are identified by the neural network model, and a confidence factor is produced by the model. In step 718 the results of neural network model analysis and colorflow are correlated to see if they agree, with an eye toward the neural network analysis confidence factor and, if the correlation is sufficiently high, the comparison is confirmed; no change is made to a pixel believed to be valid (e.g., tissue, plaque, or bloodflow), and artifact pixels are removed, the latter being done in step 720 by the artifact filter.

Variations of the system and method described above will readily occur to those skilled in the art. The neural net model can be used to recognize the carotid artery in the images, as explained in the aforementioned patent application number [2016PF00940], the contents of which are hereby incorporated by reference. Thus, a deep learning model can be used to both identify the target anatomy and to improve the quality of the image for diagnosis. Diagnostic decision support can be implemented by combining previous patient history information, anatomy identification, and anatomical measurements. This data can be processed by deep learning algorithms to provide diagnostic decision support results, confirming a diagnosis.

Figure 8:
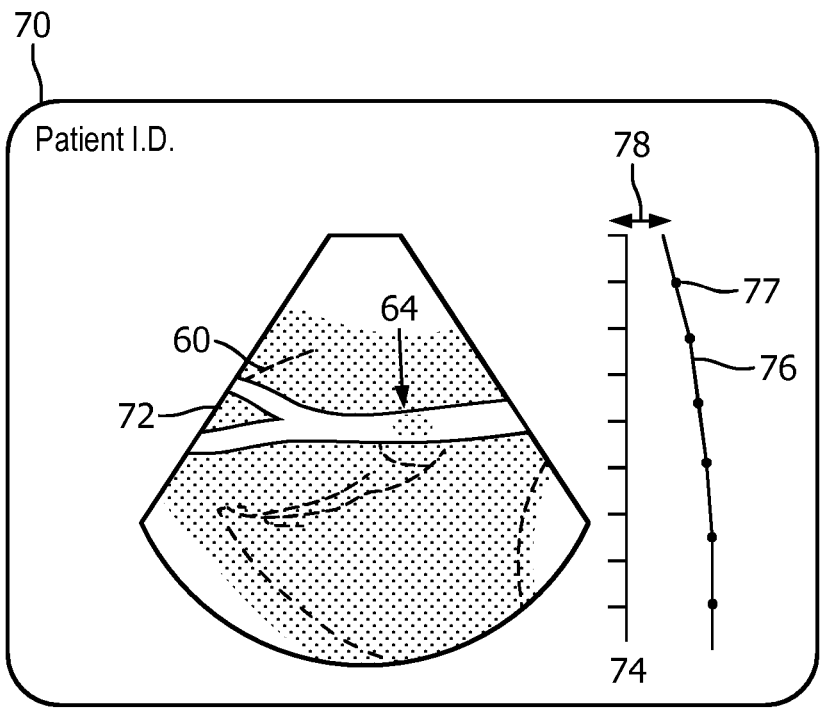
FIG. 8 illustrates an ultrasound display with an image exhibiting blood vessel clutter and a TGC curve displayed adjacent to the image.

In clinical practice prior to the advent of the present invention, sonographers have generally employed TGC adjustment to try to attenuate the haze and clutter pixels in an image and thus reduce its appearance in images. For example, FIG. 8 illustrates an ultrasound display 70 which is displaying an ultrasound image 72 of a carotid artery 60. Immediately to the right of the image is a depth scale 74 delineating increments of depth from the top (skinline) to the bottom of the image, generally in centimeters. To the right of the depth scale is the TGC curve 76, illustrating the currently applied time gain control characteristic. Portions of the curve which are leftmost (closest to the depth scale) indicate low applied gain at those depths, and portions of the curve which are rightmost have the greatest applied gain. Shown on the curve are dots or control points 77, each of which corresponds to an electronic or mechanical slidepot control. Sometimes the slidepots are mounted to the right of the display in line with the control points 77, so the user immediately can see which slidepot affects which depth. In this example the topmost slidepot of a vertical assembly of slidepots will control the position of the uppermost control point, and hence the gain at the shallowest depth of the image. Moving the slidepot to the left will reduce the gain and the control point 77 will move to the left as indicated by control arrow 78. Correspondingly, moving the slidepot to the right will increase the gain at that slidepot depth. In the example of FIG. 8, the slidepots are set to apply relatively low gain at shallow depths and relatively greater gain at deeper depths. The image of the blood vessel 60 in this example is seen to be contaminated by haze or clutter 64 in the blood vessel. The current practice for a sonographer would be to slide the slidepot at the depth of haze or clutter 64 to the left, trying to reduce the signal gain at that depth and hence the appearance of the haze or clutter in the image.

Figure 9:
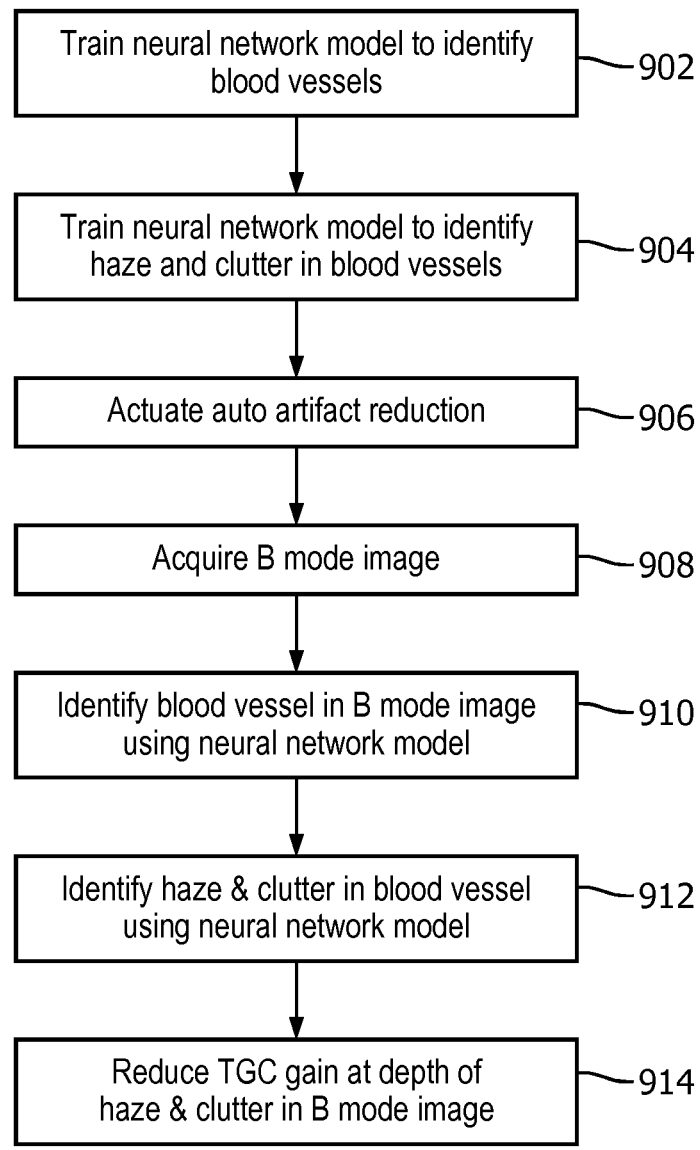
FIG. 9 is a flowchart illustrating a technique for removing blood vessel clutter in the image of FIG. 8 by adjusting the TGC characteristic.

An implementation of the present invention can use the neural network model 80 to perform this clutter reduction automatically. A technique for doing so is shown in FIG. 9. Prior to the ultrasound exam, the neural network model is trained to identify blood vessels such as the carotid artery in ultrasound images, as indicated at 902 and described above. In step 904 the neural network model is trained to identify haze and clutter in blood vessels in ultrasound images. This training can be combined if desired by training the neural network model to identify haze and clutter which appears in blood vessels in ultrasound images as indicated by step 904. When a user wants to have the ultrasound system perform this image improvement automatically, the user actuates the automatic artifact reduction feature of the ultrasound system as indicated in step 906. The user acquires a B mode image in step 908 and the ultrasound system automatically identifies a blood vessel in the image using the neural network model 80 as indicated at 910, and in step 912 the neural network model identifies haze or clutter in an identified blood vessel. When haze or clutter is identified, the TGC gain at the depth of the artifact in the image is reduced to diminish the appearance of the haze or clutter in the image as shown at 914. This is shown in FIG. 1, where the neural network model 80 is shown coupled to the TGC control circuitry 19 to command a reduction in TGC gain at the depth of the artifact in the image. This adjustment can be done in an iterative fashion, with the neural network model commanding a small reduction in TGC gain, followed by reacquisition of the ultrasound image and an analysis of the new image to see if the haze or clutter artifact is still identifiable. If so, another increment of gain reduction is commanded and the process repeated until the artifact can no longer be identified as it disappears from the image. It has been found that this artifact compensation technique allows tissue structures to remain strongly visible at the depth of compensation, as tissue and plaque are typically good specular reflectors of ultrasound.

Figure 10:
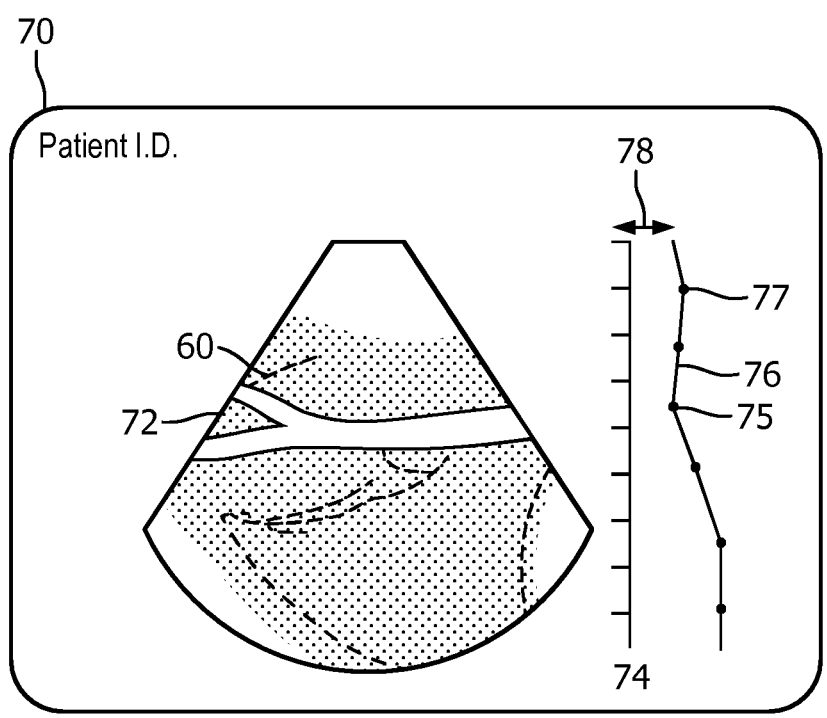
FIG. 10 illustrates the ultrasound display of FIG. 8 after clutter elimination in accordance with the technique of FIG. 9.

When this compensation has been performed by the neural network model, the ultrasound image will appear generally as shown in FIG. 10. It is seen that the haze and clutter has been eliminated but the blood vessel 60 is still clearly distinguishable in the image. This drawing also shows a resulting change to the TGC curve 76. The slidepot at the depth of control point 75 has been adjusted for reduced gain, and thus the curve is moved to the left at the depth of control point 75. To maintain a smoothly continuous curve, the gain and control points above and below the depth of control point 75 are also slightly gain-reduced as shown in the drawing, a feature commonly found in most TGC control circuitry of today's ultrasound systems.

It should be noted that an ultrasound system suitable for use in an implementation of the present invention, and in particular the component structure of the ultrasound system of FIG. 1, may be implemented in hardware, software or a combination thereof. The various embodiments and/or components of an ultrasound system, for example, the deep learning software modules, or components and controllers therein, also may be implemented as part of one or more computers or microprocessors. The computer or processor may include a computing device, an input device, a display unit and an interface, for example, for accessing the Internet as shown in FIG. 1. The computer or processor may include a microprocessor. The microprocessor may be connected to a communication bus, for example, to access a PACS system or the data network for importing training images. The computer or processor may also include a memory. The memory devices such as the image memory 28 and the ensemble memory 50 may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" or "workstation" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine.

The set of instructions of an ultrasound system including those controlling the acquisition, processing, and transmission of ultrasound images as described above may include various commands that instruct a computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules such as a neural network model module, a program module within a larger program or a portion of a program module. The software also may include modular programming in the form of object-oriented programming. The processing of input data by the processing machine may be in response to operator commands, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. An ultrasonic diagnostic imaging system for improving the image quality of ultrasound images using deep learning comprising:
    an ultrasound probe adapted to acquire ultrasound image signals;
    a B mode image processor, coupled to the probe, which is adapted to produce B mode ultrasound images;
    a neural network model, coupled to receive the B mode ultrasound images, and adapted to identify artifacts in a blood vessel in the B mode ultrasound images;
    time gain control circuitry, coupled to receive the ultrasound image signals, wherein the time gain control circuitry is adapted to be responsive to the identification of artifacts to reduce gain at an image depth of identified artifacts; and
    a display adapted to display the B mode images with reduced artifact content.

2. The ultrasonic diagnostic imaging system of claim 1, further comprising a motion detector, coupled to the probe, which is adapted to produce information about motion in the region imaged by the B mode ultrasound images, wherein the neural network model is further adapted to use information about motion in the identification of artifacts.

3. The ultrasonic diagnostic imaging system of claim 2, further comprising an artifact filter, coupled to receive the B mode images and adapted to be responsive to the neural network model to reduce artifacts identified in the B mode ultrasound images.

4. The ultrasonic diagnostic imaging system of claim 3, further comprising a correlator, responsive to analysis of B mode images by the neural network model and to the information about motion, and having an output coupled to the artifact filter adapted to control the artifact filter.

5. The ultrasonic diagnostic imaging system of claim 3, wherein the neural network model is further adapted to produce a confidence factor for display to a user.

6. The ultrasonic diagnostic imaging system of claim 1, wherein the neural network model is further adapted to recognize anatomy in the B mode image.

7. The ultrasonic diagnostic imaging system of claim 2, wherein the motion detector further comprises a Doppler processor.

8. The ultrasonic diagnostic imaging system of claim 7, wherein the Doppler processor is further configured to operate with ensemble lengths shorter that six samples.

9. The ultrasonic diagnostic imaging system of claim 7, wherein the Doppler processor is further configured to operate with ensembles acquired by multiline reception.

10. The ultrasonic diagnostic imaging system of claim 2, wherein the motion detector is further configured to operate by speckle tracking.

11. The ultrasonic diagnostic imaging system of claim 1, wherein the neural network model is further coupled to the time gain control circuitry, and adapted to communicate to the time gain control circuitry the image depth of an identified artifact.

12. The ultrasonic diagnostic imaging system of claim 1, wherein the neural network model is further adapted to reduce TGC gain and analyze a reacquired ultrasound image for artifacts in an iterative manner.

* * * * *